United States Patent [19]

McGinnis

[11] Patent Number: 5,002,050
[45] Date of Patent: Mar. 26, 1991

[54] MEDICAL GAS FLOW CONTROL VALVE, SYSTEM AND METHOD

[76] Inventor: Gerald E. McGinnis, 131 Kelvington Dr., Monroeville, Pa. 15146

[21] Appl. No.: 309,006

[22] Filed: Feb. 7, 1989

Related U.S. Application Data

[63] Continuation of Ser. No. 908,271, Sep. 17, 1986, abandoned.

[51] Int. Cl.⁵ .............................................. A61M 16/00
[52] U.S. Cl. ........................... 128/204.18; 128/204.26; 128/205.24
[58] Field of Search ....................... 128/205.24, 204.26, 128/203.11, 206.15, 207.12, 207.16, 911, 204.18, 204.27, 204.29; 137/852, 854, 859

[56] References Cited

U.S. PATENT DOCUMENTS

| | | | |
|---|---|---|---|
| 2,747,572 | 5/1956 | Gagnan | 128/207.16 |
| 2,887,104 | 5/1959 | Sovinsky et al. | 128/203.11 |
| 3,286,710 | 11/1966 | Bartlett | 128/203.11 |
| 3,356,100 | 12/1967 | Seeler | 128/203.11 |
| 3,527,242 | 9/1970 | Ansite | 137/854 |
| 3,630,197 | 12/1971 | Hirano et al. | 128/204.26 |
| 3,795,257 | 3/1974 | Fabish et al. | 128/204.26 |
| 3,995,625 | 12/1976 | Needham | 128/204.26 |
| 4,501,271 | 2/1985 | Clifton et al. | 128/205.24 |
| 4,694,825 | 9/1987 | Slemmer et al. | 128/205.24 |

FOREIGN PATENT DOCUMENTS 1447091  8/1976  United Kingdom .......... 128/205.24

Primary Examiner—Lee S. Cohen
Assistant Examiner—J. P. Lacyk
Attorney, Agent, or Firm—Carothers & Carothers

[57] ABSTRACT

An exhaust valve and method for use in medical ventilation and anesthesiology therapy wherein the valve combines gas delivery and controlled exhalation or exhaust functions; also certain medical gas administering systems incorporating the novel valve and method.

10 Claims, 3 Drawing Sheets

MEDICAL GAS FLOW CONTROL VALVE, SYSTEM AND METHOD

This is a continuation of co-pending application Ser. No. 908,271, filed on Sept. 17, 1986, now abandoned.

BACKGROUND OF THE INVENTION

In the medical arts there are known a variety of systems for assisted ventilation of patients and for administration of anesthetic gas. With prior art ventilation apparatus, a patient typically is ventilated by an electromechanical ventilator which delivers oxygen enriched air to the patient on a predetermined, programmed basis. Examples of prior ventilation techniques include CPAP, assisted or controlled ventilation and intermittent mandatory ventilation, among others. With many prior cyclically operating ventilation systems, the patient's lungs are ventilated by cycling airway pressure between ambient atmospheric pressure and some higher ventilation pressure. During the high pressure phase of the cycle, the lungs are inflated with the breathing gas mixture supplied by the system. During the ambient pressure phase, the lungs deflate as the patient spontaneously exhales the gas into the atmosphere or other suitable exhaust facility. With CPAP therapy, a continuous positive pressure is superimposed on the ambient pressure phase, as is well known.

Prior ventilation system tubing circuits commonly include a gas supply side and an exhaust or exhalation side, and patient airway pressure is controlled by an exhalation valve which is installed in-line with the exhalation side of the tubing circuit. Prior exhalation valves typically have been controlled by a control pressure generated by the ventilator apparatus independently of the gas supply pressure. The control pressure is effective, when the ventilator begins an inhalation cycle, to close the exhalation valve and allow the pressure in the circuit to be elevated to the desired airway pressure. The patient thus experiences assisted inhalation. When the ventilator stops positive pressure gas delivery, the exhalation valve control pressure is reduced to permit elevated patient airway pressure to open the exhalation valve and the patient thus exhales through the exhalation valve.

Another known ventilatory therapy controller is the PEEP valve, which may be used in conjunction with the exhalation valve in order to maintain exhalation pressure at a pressure higher than ambient and thereby keep the lungs under positive pressure throughout the exhalation phase of the cycle. Positive expiratory pressure has also been obtained by controlling the exhalation valve itself to provide positive expiratory pressure.

Among the more common medical gas delivery circuits are the conventional circle anesthesia system and partial rebreathing anesthesia or resuscitation systems. Among the prior art patents known to the applicant which pertain to valves for respiration and anesthesia apparatus generally, are the following: U.S. Pat. No. 3,017,881 shows a system for administering anesthesia to a patient wherein the patient inhales a gas mixture including an anesthetic and exhales through a conduit leading to an exhaust valve. Others include U.S. Pat. Nos. 4,502,502; 4,044,793; 4,037,595; 3,800,793; 3,721,239; and 2,868,198, and French Patent No. 2,003,192.

Although the conventional systems have generally served their intended purposes, practitioners of the art continue to seek improved systems offering enhanced economy, reliability and ease of maintenance and operation. For example, in common usage, the external valve and tubing circuitry of a ventilator circuit often may have to be changed on a daily or perhaps semi-daily basis in order to minimize the possibility of bacterial growth within the system which could infect or reinfect the patient. Frequent replacement of conventional circuits is rather expensive as the circuitry often comprises substantial lengths of tubing and multiple valves which must be either cleaned up for reuse or discarded and replaced with new valve and tubing circuitry.

Another shortcoming of many prior ventilation systems is that, due to the necessary valving arrangements they include relatively long lengths of tubing in separate air supply and exhaust legs. This compounds the difficulties that are inherent in determining the patient's tidal volume and lung-thorax compliance, determinations which must be accurate to ensure proper adjustment and programming of the ventilator to provide the most thereputically beneficial ventilatory assistance. Excess tubing lengths introduce both an enlarged working volume of air in the tubing circuitry, and an increment of system compliance, similar to lung compliance, as the resiliently flexible tubing is cyclically distended and relaxed in response to the pressure variations imposed during the ventilation cycle. These variables are superimposed on the parameters of lung mechanics of the patient, and their impact must be fully appreciated and taken into account before the ventilation cycle can be properly programmed.

Another conventional anesthesia system includes a manual breathing bag which the physician squeezes to ventilate the patient. Manual squeezing of the breathing bag increases the system supply pressure sufficiently to close the exhaust valve and thereby force the system gas mixture into the patient's lungs. When the physician releases the breathing bag, the exhaust valve is permitted to open again. Such systems may often includes a pressure relief valve connected to the anesthesia scavenging system, that may be manually adjusted to open only if the pressure in the system exceeds a predetermined valve setting during system operation. For such systems, the physician may manually ventilate the patient by first adjusting the relief valve to increase its pressure relief set point so that sufficient pressure can be applied by squeezing the breathing bag for the desired ventilation without opening the relief valve. The relief valve must be readjusted after patient ventilation.

Even in systems which do not accommodate such manual ventilation, but instead merely provide a gas mixture at a constant volume flow rate for unassisted breathing by the patient, a relief valve is provided to relieve pressure excursions resulting from discontinuities between the gas supply rate and the patient's gas consumption and breathing rate. Improper adjustment of the relief valve can result in system supply pressure excursions of dangerous proportions.

BRIEF SUMMARY OF THE INVENTION

The present invention contemplates a novel control valve which incorporates both gas supply and exhaust control functions in a single valve assembly, and medical gas administering systems incorporating same, wherein the valve is so structured to operate according to a method wherein the gas delivery pressure from the ventilator in the supply line of the ventilator system functions to control opening and closing of the exhaust or exhalation port of the valve. The valve thus permits the elevated pressure gas supply flow to bypass the exhalation port of the valve and to pass through the valve to the patient's airway as the gas supply pressure, acting on respective pressure actuated control surface areas of the valve, is effective to keep the exhalation port closed. During the exhalation portion of a ventilation cycle, the pressure actuated control surface areas will respond to a very small pressure differential between supply pressure and patient airway pressure to permit initiation of substantially passive exhalation to ambient atmospheric pressure, or to a vacuum (i.e. scavenging) facility.

The novel valve preferably comprises a unitary valve structure that permits novel and improved ventilation and anesthesia gas flow circuitry to be used. For example, in one novel system incorporating the valve of this invention, a circle type anesthesia system is provided with the novel valve at a point directly adjacent to the patient supply interface (e.g. a mask or endotracheal tube) and is effective to provide automatic exhaust valve closing during manual ventilation and assured exhaust valve opening under any patient airway pressure excursion initiated by patient exhalation effort.

Another novel system of this invention is a simplified partial rebreathing anesthesia or resuscitation system incorporating the novel valve in-line intermediate the patient supply interface and a manual breathing bag. Still another novel system of this invention is a simplified CPAP system incorporating the novel valve in-line intermediate the gas supply/PEEP junction and the patient supply interface. In each novel system the novel valve is interposed in-line between the patient supply interface and a gas supply source which is capable of supplying medical gas to the patient under pressure. The gas supply source may be an external source of constant rate gas flow or constant pressure gas flow, a manual breathing bag, or any of a variety of other sources. The gas from the source passes through the novel valve to the patient supply interface as the supply pressure serves to close the exhaust port of the valve. The actuating surfaces of the novel valve are proportioned to provide a balanced valve actuating structure which is effective to operate the valve under very small actuating pressure differentials.

It is therefore one general object of the invention to provide a novel and improved control valve for use in a medical gas supply apparatus such as a ventilator or anesthesia administering apparatus.

A more specific object of the invention is to provide, for a ventilation or anesthesia system, or other medical gas administering apparatus, a novel and improved control valve having an inlet which is adapted to communicate with a source of gas flow, an outlet which is adapted to communicate with the airway of a patient, and an exhalation port which is isolated by the action of gas supply pressure from both the inlet and outlet of the valve during an inhalation portion of a ventilation cycle. According to the novel method, during inhalation the patient receives gas from the gas supply apparatus via the control valve. The exhalation port is maintained in communication with the outlet of the valve throughout the exhalation portion of the ventilation cycle through the action of a pressure differential between gas supply pressure in the valve inlet and the patient's airway pressure exerted in the outlet of the valve.

A further object of the invention is to provide novel ventilator tubing and flow control circuitry incorporating a control valve as above characterized.

These and other objects and further advantages of the invention will be more clearly understood upon consideration of the following detailed description, and the accompanying figures, in which.

Figures 1, 2:
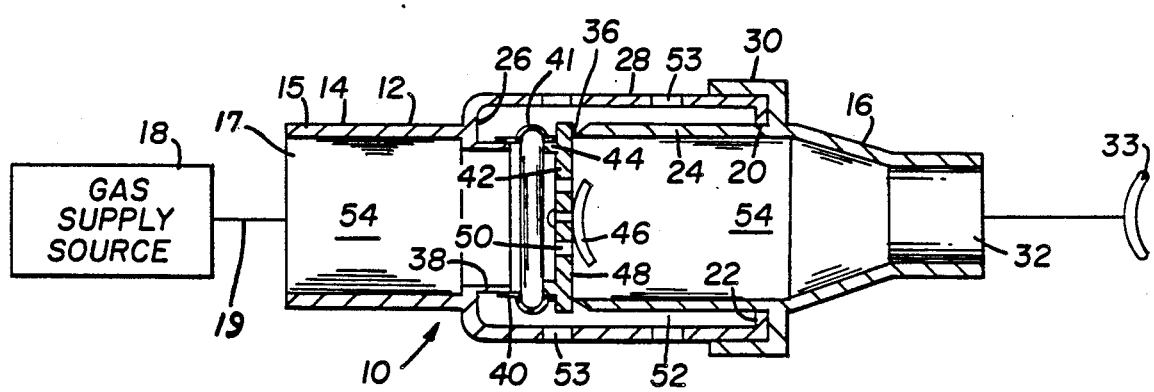
FIG. 1 is a sectional side elevation of a valve according to the present invention showing the gas supply port open and the exhalation port closed.
FIG. 2 is a fragmentary portion of FIG. 1 showing the exhalation port of the valve open.

There is generally indicated at 10 in FIG. 1 a control valve constructed according to one presently preferred embodiment of the instant invention and comprised of a valve body 12 that is made up of two coaxially interfitted, generally cylindrical body members 14 and 16. Body member 14 comprises an outer open end 17 which forms the inlet end of valve 10 and is adapted for connection to a source of pressurized gas flow as indicated at 18. An inner open end 20 of body member 14 is formed by a radially inwardly projecting flange 22 to receive a complementary end portion 24 of body member 16 coaxially therein. Intermediate the open ends 17 and 20, body member 14 includes a smaller diameter inlet end portion 15 and a diametrically enlarged cylindrical exhaust plenum portion 28 thereof. Flange 22 is formed adjacent the outer longitudinal end of exhaust plenum 28, and an annular step 26 adjacent the opposite longitudinal end thereof joins exhaust plenum 28 coaxially to inlet end portion 15.

The inner end portion 24 of body member 16 is of an axially elongated cylindrical form with an outer diameter that permits a sliding fit thereof coaxially within flange 22 such that, for assembly of valve body 12, end portion 24 is interfitted coaxially within exhaust plenum 28 and is secured with respect thereto by such means as a suitable bonding agent applied in the interface between flange 22 and inner end portion 24. For example, the body members 14 and 16 may be polystyrene plastic and the bonding agent a suitable solvent welding bonding agent.

To provide a stronger and more rigid valve body assembly, body member 16 may be provided with a radially outwardly and axially projecting flange portion 30 to circumferentially encompass and axially overlap flange 22 and adjacent portions of exhaust plenum 28. A suitable bonding agent would thus also be applied throughout the interfacing surface portions of flange 30 and the complementary surface portions of flange 22 and exhaust plenum portion 28 to provide a rigidly bonded, unitary structure. Of course, there are numerous alternative design configurations for the bonded interfacing portions of members 14 and 16, the structure shown in FIG. 1 being merely exemplary.

The outermost open end 32 of member 16 projects axially outward of member 14 and is adapted for connection to an appliance utilized for directing gas flow and pressure into the airway of a patient, for example a face mask 33. The opposite or inner end portion 24 of member 16 projects axially within exhaust plenum 28, as described, and terminates therein to form an annular valve disk seat 36 that is located axially intermediate the ends of exhaust plenum 28.

Member 14 includes, radially inwardly adjacent to step 26, an integrally formed cylindrical flange 38 which projects coaxially within member 14 toward valve disk seat 36. A resliently flexible, generally cylindrical mushroom type diaphragm 40 is sealingly mounted in encompassing relationship on flange 38 and projects axially therefrom toward valve seat 36. Diaphragm 40 is sealingly secured in coaxially encompassing relationship about a circular flange portion 44 of a rigid valve disk 42 such that valve disk 42 is supported by diaphragm 40 in coaxially adjacent relationship with valve seat 36. The longitudinal flexibility of diaphragm 40, afforded by a formed enlarged diameter bellows portion 41 thereof, permits very small pressure differentials between the opposite sides of disk 42 to move the disk 42 axially into and out of seated engagement with valve seat 36, as more fully described hereinbelow.

A resiliently flexible check valve disk 46 is affixed coaxially on the downstream side 48 of valve disk 42 in overlapping relationship with a plurality of axial through openings or ports 50 which penetrate valve disk 42 within the area encompassed by diaphragm 40 and seat 36. Ports 50 and flexible disk 46 thus cooperate to provide a one-way flow check valve which permits gas flow via ports 50 to the right (FIG. 1) by flexing of peripheral portions of disk 46. Of course, gas cannot flow in the opposite direction due to resultant sealing of the flexible disk 46 against surface 48 to close the ports 50.

An axially elongated, annular exhaust chamber 52 is formed by plenum 28 and the inner end portion 24 of member 16, and by disk 42, diaphragm 40 and flange 38. A plurality of radially extending through openings 53 penetrate plenum 28 to provide open communication between chamber 52 and the exterior of valve 10.

As will be seen, when valve disk 42 is seated upon valve seat 36 (FIG. 1), exhaust chamber 52 is isolated from the gas flow passage 54 which extends axially through valve 10, and when valve disk 42 is displaced axially from seat 36 (FIG. 2), chamber 52 is open to gas flow passage 54.

The disclosed valve 10 is suitable for gas flow valving functions in a variety of ventilation and anesthesia circuits. In any such system to which the valve 10 is applied, control of exhaust flow is afforded by the supply pressure originating upstream of the valve 10 (e.g. in source 18), and reaching valve 10 via the primary gas flow supply conduit 19 connecting source 18 to inlet end portion 15 of the valve 10.

For proper operation of valve 10, according to my novel method the effective actuation areas on opposite sides of the disk 42 are proportioned to ensure that disk 42 remains seated on seat 36 when gas pressure is equal on the opposite sides of disk 42. That is, in the illustrative FIG. 2, area $A_1$ is incrementally larger than area $A_2$. Thus, with equal gas pressure on opposite sides of disk 42, a small net force differential urging disk 42 into seated engagement with seat 36 is maintained, and exhalation or exhaust chamber 52 thereby remains isolated from gas flow passage 54. Accordingly, at any positive pressure gas flow can proceed from source 18 and conduit 19 through valve 10 via passage 54 (by passing through check valve ports 50) and thence to the patient via face mask 33.

A reverse gas flow impetus of any magnitude, for example, as caused by patient exhalation effort, will urge disk 42 to the left and simultaneously close check valve disk 46 (FIG. 2), thus directing reverse flow to pass into chamber 52 and via ports 53 into the ambient atmosphere, rather than back flowing toward source 18. The gas pressure differential required to move disk 42 is extremely small due to the high degree of flexibility of diaphragm 40.

Thus, according to my novel method, in valve 10 the effective actuating areas on opposite sides of disk 42 are balanced by design to provide optimal performance, which is attained when only very slight pressure differentials are required to actuate the valve. If the pressure in outlet end 32 exceeds the pressure in inlet end 15 by as little as ½ centimeter of water to 1 centimeter of water, disk 42 will open and reverse flow will pass via exhalation ports 53 from valve 10. In this manner, a ventilator cycling between high inhalation pressure and low exhalation pressure, if connected to inlet end 15 of valve 10, will cause the patient's lungs to be inflated whenever the ventilation pressure is higher than or equal to the pressure at outlet 32, which will at all times correspond closely to patient airway pressure. When the ventilator cycle enters the exhalation phase, patient airway pressure will be higher than inlet end 17 pressure and disk 42 thus will be lifted from seat 36. The patient then will be able to exhale through the exhalation ports 53. In this manner, the patient's lungs can be ventilated without using a separate exhalation valve and exhalation tubing circuit. Rather, exhalation is achieved by back flowing the exhaled gas through a forshortened portion of the primary gas supply leg of the tubing circuit to the exhaust ports of valve 10.

As mentioned above, the described valve may be employed to provide a variety of novel medical gas supply or administering circuits. For example, in FIG. 3 there is shown a partial-rebreathing anesthesia or resuscitation apparatus with a modified embodiment of the control valve shown at 10'. The apparatus of FIG. 3 comprises the valve 10' having the outlet end 32 thereof connected via a conduit 60 to a mask 33 for supplying medical gas to a patient. A supply of fresh gas (e.g. anesthetic) is provided from a source 62 via a conduit 64 to a junction 66 with conduit 60.

Valve 10' is constructed substantially as the above-described valve 10, but in addition is provided with an outer plenum 68 which encompasses the exhaust plenum 28 and valve inlet end portion 15, and extends longitudinally thereof. A breathing bag 70 is connected to an elongated open ended extension 69 of plenum 68 so as to communicate openly with the gas supply flow passage 54 within valve 10' and selectively with the interior space 72 of plenum 68. To this end, plenum 68 is provided with a plurality of axial extending openings 74 distributed about one longitudinal end thereof to provide gas flow communication between space 72 and the interior of extension 69. A one way flow check valve element such as falp valve 73 overlies each opening 74 to permit gas flow only in the direction from space 72 to breathing bag 70.

At the opposite longitudinal end of plenum 68, one or more openings 76 provide gas flow communication between space 72 and the interior of an annular scavenging plenum 78. Each opening 76 is provided with a lightly spring loaded pressure relief valve 77 which permits gas flow from space 72 into scavening plenum 78 only when the pressure in space 72 exceeds a predetermined set pressure, for example 2 to 3 cm H₂O. Additional openings 80 in scavenging plenum 78 provide communication between the ambient atmosphere and the interior of scavenging plenum 78 to serve as draft ports. The scavenging system 82 is connected to plenum 78 as shown at 75 to operate at a small negative pressure, on the order of 2 to 3 cm H₂O.

The system of FIG. 3 functions in accordance with my novel method as follows. A continuous, constant rate flow of gas is provided via conduit 64 from source 62 to mask 33 and then to the patient. When the patient is not inhaling vigorously, the pressure of the gas supplied opens disk 42 of valve 10' to permit gas to backflow into space 72 and thence via ports 74 to breathing bag 70. During spontaneous patient respiration, exhalation also produces such gas backflow whereas, during inhalation, patient gas demand in excess of the supply rate from source 62 is satisfied by gas being drawn from breathing bag 70 via the check valve ports in disk 42. Flap valves 73 prevent gas flow from breathing bag 70 into space 72 and connected spaces.

The breathing bag may of course be manually squeezed to force gas therefrom into the lungs of the patient. Such manual ventilation does not require any adjustment of the exhaust valve as the supply pressure controls the movement of exhaust valve disk 42. Furthermore, because only the smallest gas pressure differential over supply pressure will open the exhuast valve disk 42, it is not possible for the exhaust valve disk to lock up in a closed configuration and thereby permit dangerous pressure excursions in the system.

The scavenging system 82 operates at a very low partial vacuum pressure, 2 to 3 cm H₂O as mentioned, for example, and is always able to draw via draft ports 80. Accordingly, the scavenging system operates effectively without imposing any signficant pressure variance on the anesthesia supply system. The scavenging system 82 thus removes from the system any excess gas which reaches plenum 78 via value 77. In particular, during patient exhalation, the scavenging system 82 will take all excess gas flow beyond that which can be accommodated by inflation of breathing bag 70 as the resultant pressure increase in space 72 will open valve 77 and permit the excess gas to flow into the plenum 78.

Figure 4:
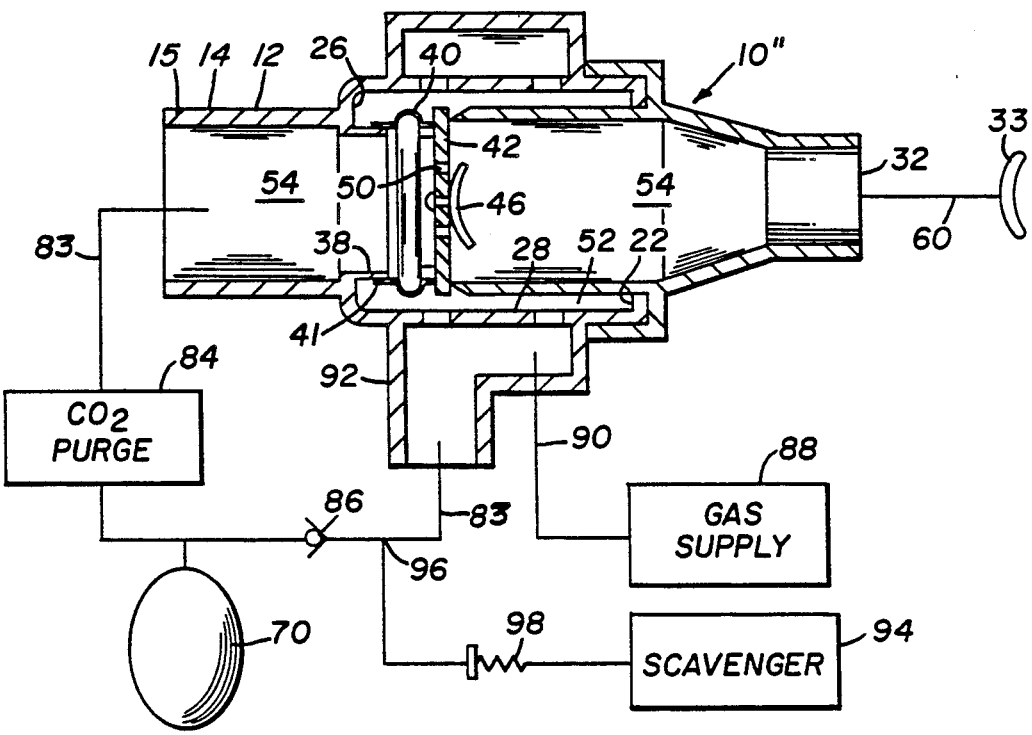
FIG. 4 is a simplified schematic illustration of a circle type anesthesia system of the present invention.

Another novel system for use with a modified valve 10'' is of the form of a so-called circle type anesthesia system in which a conduit 83 is connected to the inlet end 15 of valve 10'' to carry gas thereto from breathing bag 70 via a purge system 84 (FIG. 4). Another leg of the conduit 83 provides a gas flow path from the exhaust side of valve 10'', via a one way flow check valve 86, to breathing bag 70. A source of gas flow 88 (e.g. anesthesia) is also connected via a conduit 90 to the exhaust side of valve 10''. To accommodate connection of conduits 83 and 90 to the exhaust side of valve 10'', the valve is provided with a plenum 92 that encompasses the above-described plenum 28 of the valve 10.

Intermediate check valve 86 and plenum 92, a scavenging system 94 is connected to conduit 83 as at 96. Reverse flow from scavenging system 94 into the anesthesia system may be prevented by, for example, a spring loaded one way flow check valve 98.

From the above description, it will be seen that the circle anesthesia system of FIG. 4 is operable in accordance with my novel method to provide a one way flow circuit in conduit 83 such that patient inhalation draws air via purge system 84 from breathing bag 70, with fresh anesthetic introduction via conduit 90 from source 88. Patient exhalation lifts the valve disk 42 and directs gas flow via pelnum 92 through conduit 83, via check valve 86, and into breathing bag 70. The continuous flow from source 88 via conduit 90 serves to entrain anesthetic gas in the exhalation flow to bag 70 for delivery to the patient during subsequent inhalation. Scavenger system 94 operates to collect and dispose of all gas flow exceeding the effective working volume of the system plus the patient's tidal volume.

In yet another novel system incorporating the valve 10, a CPAP supply system 100 (FIG. 5) is connected via conduit 102 to the inlet end 15 of valve 10. The outlet end 32 of valve 10 is connected to mask 33 as above described. A PEEP valve or similar control valve 104 is connected to conduit 102 to provide release of supply pressure which could otherwise increase beyond desired limits during exhalation. In accordance with my novel method, the elevated pressure thus maintained in conduit 102 is effective, during exhalation, to keep disk 42 closed (i.e. seated on seat 36) until a predeterminable level of patient exhalation effort is exerted. Precisely limited positive exhalation pressure is thereby maintained; however, the patient exhales to the ambient atmosphere, not to a pressurized reservoir or gas collection facility.

Figure 6:
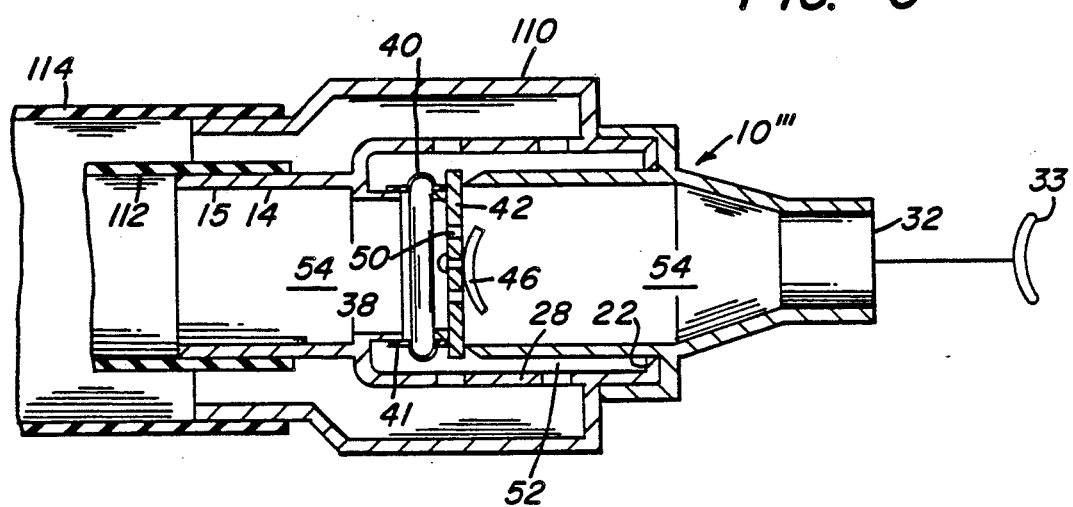
FIG. 6 is a sectioned side elevation of an additional tubing network configuration according to the present invention.

In the above described systems, as in others, the tubing network connected to the inlet end 15 of valve 10, and any tubing connected to the exhaust ports of the valve, may be coaxially arranged as shown in FIG. 6. There, the valve 10''' includes the valve substantially as above-described, and including in addition an exhaust pelnum 110 which encompasses valve body member 14 and extends axially thereof toward the inlet end 15. The coaxial tubing arrangement includes an inner supply tube 112 connected to supply end 15 and an encompassing outer exhaust gas conveying tube 114 connected to the open end of plenum 110. This arrangement may serve such purposes as improved economy, enhanced simplicity through reduction of the number of separate tubing runs required, thermal insulation of the inner supply tube 112, or heat transfer between the gases flowing in outer exhaust tube 114 and inner supply tube 112.

Figure 3:
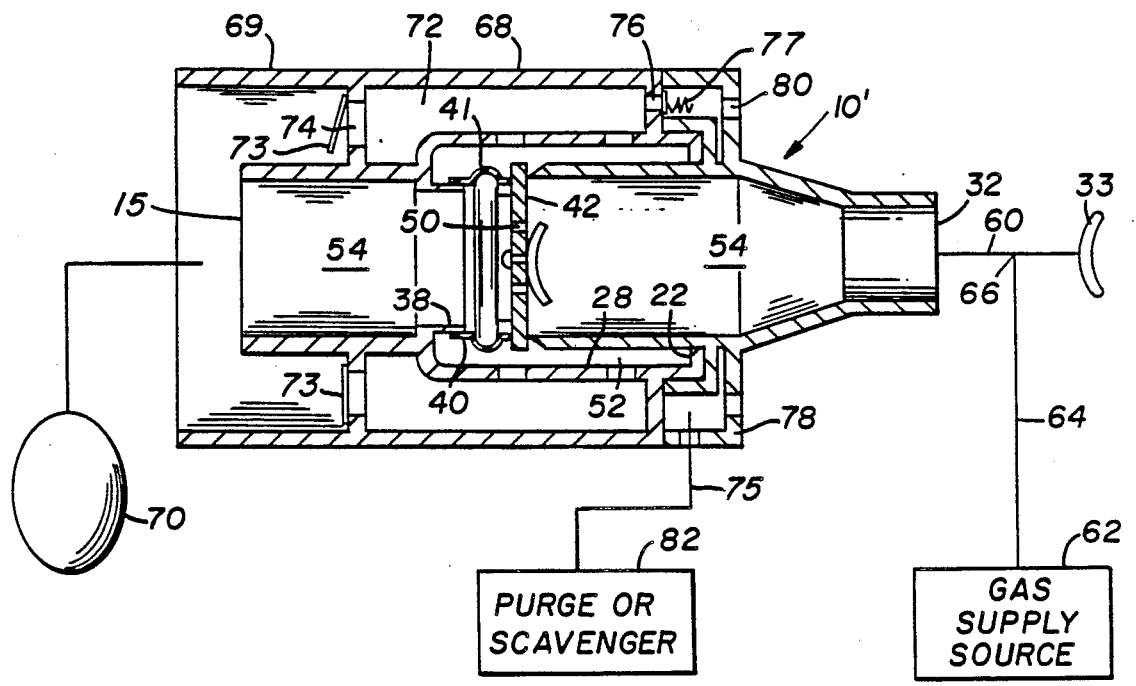
FIG. 3 is a simplified schematic illustration of a partial rebreathing anesthesia or resuscitation system according to the present invention.
Figure 5:
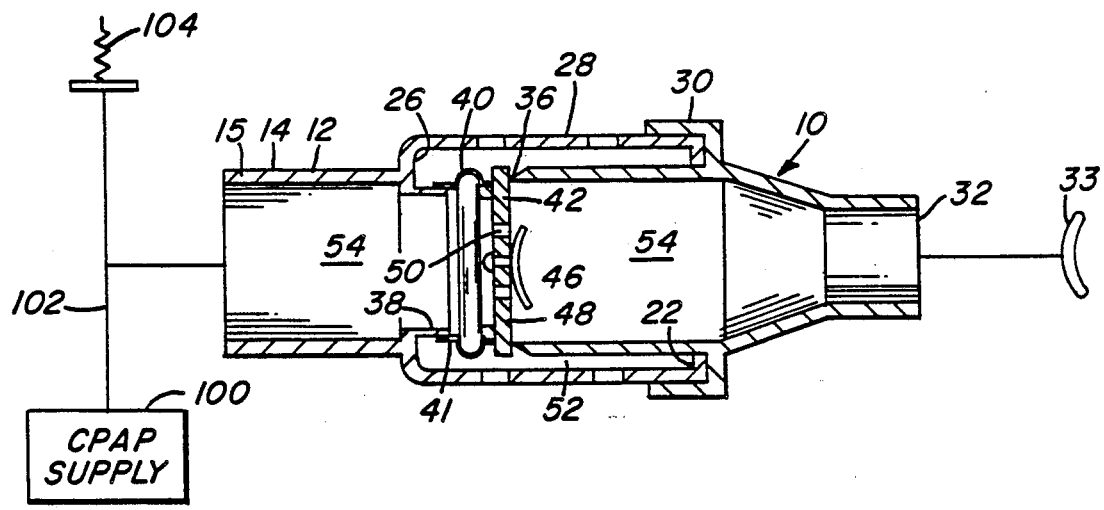
FIG. 5 is a simplified schematic illustration of a CPAP ventilation system of the present invention.

According to my novel method, in each of the systems of FIGS. 3, 4, and 5, exhaust valve actuating or opening is passivly controlled by the supply pressure and is operated in conjunction with closing of the supply line backflow check valve. Accordingly, any supply pressure of even the smallest significant magnitude will be effective to close the exhaust and permit reliable gas supply to the patient via the valve supply passage 54. Likewise, any backflow pressure impetus of even the smallest significant magnitude will be effective to close the supply backflow check valve and lift the valve disk to thereby open the exhaust ports to exhaust flow.

Of course, ordinarily there may be several other connections for access to the disclosed circuits for pressure, temperature or humidity sensing, gas sampling, and the like. These are not shown in the drawings as their functions and operation are well known.

Because of the need to prevent infection or reinfection of the patient, entire circuits typically must be discarded and replaced at least on a daily basis. The initial cost and replacement cost of the circuitry are considerable because of the long lengths of tubing utilized and the cost of the conventional exhalation control valve. Thus, the invention provides a substantial economic benefit by combining control valve functions and thereby minimizing the replacement cost of both the valving elements, and the connecting tubing runs.

According to the description hereinabove, the present invention provides a novel and improved control valve and novel medical gas administering systems and method wherein the gas supply pressure, acting through the primary supply or inhalation flow path is effective to control valve operation to thereby control inhalation and exhalation flow in such systems.

Of course, I have contemplated various modified and alternative embodiments of the invention which would also readily occur to others versed in the art once apprised of my invention. Accordingly, it is intended that the invention be construed as broadly as permitted by the scope of the claims appended hereto.

I claim:

1. In a system adapted to provide a regimen of respiratory therapy to a patient by providing medical gas to a patient via a flow passage including an exhalation valve, the method of controlling exhalation by the patient comprising the steps of:
   providing a continuous supply of medical gas at positive pressure via said flow passage to the airway of the patient for inhalation and exhalation of the medical gas by the patient;
   disposing of gas exhaled by the patient via said exhalation valve;
   providing a valve element having a pair of opposed surface areas and being movably disposed in said flow passage within said exhalation valve to be effective for opening said exhalation valve to dispose of the gas exhaled by the patient upon initiation of exhalation effort by the patient exceeding said positive pressure; and
   applying the positive pressure of said supply of medical gas directly through said flow passage to unequal surface area portions of said opposed surface areas to establish a minimum level of exhalation effort which is effective to open said exhalation valve for disposal of the gas exhaled by the patient.

2. The method as claimed in claim 1 wherein said valve element is effective to open the exhalation valve for disposal of the exhaled gas upon initiation of exhalation effort exceeding said positive pressure by ½ to 1 cm H₂O.

3. The method as claimed in claim 1 wherein said positive pressure is a constant positive pressure.

4. In an apparatus for administering medical gas to a patient through repeated cycles of inhalation and exhalation, the combination for controlling the exhalation cycles of the patient comprising:
   a valve including a body having an inlet port and an outlet port, and a gas flow passage communicating between said inlet and outlet ports;
   said outlet port being adapted to be connected to the airway of the patient such that said flow passage forms a portion of a gas supply flow path through which medical gas is supplied to the airway of the patient;
   said valve body including an exhalation flow path which communicates with said gas flow passage and is adapted to be connected to an exhalation gas receiving facility to permit exhalation gas to flow from said gas flow passage to the exhalation gas receiving facility;
   valving means located in said gas flow passage and supported therein by support means in a manner to segregate said gas flow passage into an upstream portion extending between said inlet port and said valving means and a downstream portion extending between said outlet port and said valving means;
   said valving means being selectively moveable to open and close said exhalation flow path to thereby control exhalation gas flow to the exhalation gas receiving facility;
   gas supply means connected to said inlet port and operable to provide a continuous positive pressure supply of medical gas within said upstream portion of said gas flow passage;
   said valving means being operable to permit continuous application of the pressure of the medical gas within said upstream portion to said downstream portion and the airway of the patient;
   said valving means and said support means defining a differential area actuating means which is operable to move said valving means in a manner to close said exhalation flow path and block gas flow from said gas flow passage to the exhalation gas receiving facility throughout medical gas flow via said gas flow passage from said supply means to the airway of the patient; and
   said differential area actuating means being further operable to move said valving means in a manner to open said exhalation flow path to permit gas flow therethrough from said gas flow passage in response to a gas pressure within said downstream portion which exceeds said positive pressure by a given pressure differential whereby the patient exhalation effort which is sufficient to initiate exhalation flow via said exhalation flow path is controlled by the magnitude of the positive pressure of gas supplied by said gas supply means.

5. The combination as claimed in claim 4 wherein said valving means includes a one way flow check valve means which permits supply gas to flow through said valving means only from said upstream portion toward said downstream portion.

6. The combination as claimed in claim 5 wherein said valving means includes a seat means and a valve disk means disposed within said gas flow passage adjacent said seat means, said valve disk means being moveably supported by said support means within said gas flow passage for movement into and out of engagement with said seat means to selectively open and close said exhalation flow path.

7. The combination as claimed in claim 6 wherein said support means includes a resiliently flexible, generally cylindrical diaphragm means extending longitudinally of said gas flow passage from said disk means toward said inlet port.

8. The combination as claimed in claim 7 wherein the said differential area actuating means includes the effective cross sectional areas on opposed sides of said disk means and said diaphragm means which are exposed to gas pressure in said upstream and downstream portions.

9. The combination as claimed in claim 8 wherein said one way flow check valve means includes aperture means formed in said disk means and communicating between the opposed sides thereof, and a resiliently flexible valve flap means carried by said disk means and disposed thereon in overlying relationship with respect to said aperture means.

10. The combination as claimed in claim 4 wherein said given pressure differential is a pressure differential of ½ to 1 cm H₂O.

* * * * *